(12) United States Patent
Wiley et al.

(10) Patent No.: US 7,979,285 B2
(45) Date of Patent: Jul. 12, 2011

(54) SYSTEMS AND METHODS FOR ENHANCED MIN/MAX EDIT FOR DRUG CLAIM SUBMISSION VERIFICATION

(75) Inventors: Angela Saterfiel Wiley, Douglasville, GA (US); James Morgan Ringold, Lawrenceville, GA (US)

(73) Assignee: NDCHealth Corporation, Atlanta, GA (US)

( * ) Notice: Subject to any disclaimer, the term of this patent is extended or adjusted under 35 U.S.C. 154(b) by 814 days.

(21) Appl. No.: 11/744,047

(22) Filed: May 3, 2007

(65) Prior Publication Data
US 2008/0275723 A1    Nov. 6, 2008

(51) Int. Cl.
*G06Q 40/00* (2006.01)
*G06F 19/00* (2011.01)
(52) U.S. Cl. .................................. 705/2; 705/3
(58) Field of Classification Search .................. 705/2, 3
See application file for complete search history.

(56) References Cited

U.S. PATENT DOCUMENTS

| | | | |
|---|---|---|---|
| 5,628,530 A | 5/1997 | Thornton | |
| 6,012,035 A | 1/2000 | Freeman et al. | |
| 6,757,898 B1 | 6/2004 | Ilsen et al. | |
| 6,769,228 B1 | 8/2004 | Mahar | |
| 7,155,397 B2 * | 12/2006 | Alexander et al. | 705/2 |
| 2002/0002495 A1 | 1/2002 | Ullman | |
| 2002/0087583 A1 | 7/2002 | Morgan et al. | |
| 2002/0111832 A1 | 8/2002 | Judge | |
| 2002/0198831 A1 | 12/2002 | Patricelli et al. | |
| 2003/0009367 A1 | 1/2003 | Morrison | |
| 2003/0050799 A1 | 3/2003 | Jay et al. | |
| 2003/0149625 A1 | 8/2003 | Leonardi et al. | |
| 2003/0154163 A1 | 8/2003 | Phillips et al. | |
| 2003/0229540 A1 | 12/2003 | Algiene | |
| 2004/0039599 A1 | 2/2004 | Fralic | |
| 2004/0073457 A1 | 4/2004 | Kalies | |
| 2004/0078234 A1 | 4/2004 | Tallal, Jr. | |

(Continued)

FOREIGN PATENT DOCUMENTS

CA    2482370    3/2006

(Continued)

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner* — Gerald J. O'Connor
*Assistant Examiner* — Maroun Kanaan
(74) *Attorney, Agent, or Firm* — Sutherland Asbill & Brennan LLP

(57) ABSTRACT

Systems and methods are provided for verification of claims submitted by one or more pharmacies. The systems and methods include storing a Multiple Package Edit (MPE) table that includes drug package size information, storing an audit table that includes drug dose information, and storing a user table that includes pharmacy-supplied drug information. The systems and methods also include receiving a first claim submission from a pharmacy computer, where the first claim submission includes at least one identifier, a quantity, and days supply for a requested drug. The systems and methods further include determining that the first claim submission includes an error in at least one of the quantity and days supply based upon information obtained from at least one of the user table, the MPE table, and the audit table, and messaging the pharmacy computer with an indication of the determined error.

20 Claims, 7 Drawing Sheets

U.S. PATENT DOCUMENTS

| | | |
|---|---|---|
| 2004/0117323 A1 | 6/2004 | Mindala |
| 2004/0148198 A1 | 7/2004 | Kalies |
| 2004/0249745 A1 | 12/2004 | Baaren |
| 2005/0015280 A1 | 1/2005 | Gabel et al. |
| 2005/0060201 A1 | 3/2005 | Connely et al. |
| 2005/0065817 A1* | 3/2005 | Mihai et al. ................ 705/2 |
| 2005/0102169 A1 | 5/2005 | Wilson |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240473 A1 | 10/2005 | Ayers |
| 2005/0288972 A1 | 12/2005 | Marvin et al. |
| 2006/0020514 A1 | 1/2006 | Yered |
| 2006/0026041 A1 | 2/2006 | Ullman et al. |
| 2006/0106647 A1* | 5/2006 | Brummel et al. ............ 705/3 |
| 2006/0149784 A1 | 7/2006 | Tholl et al. |
| 2006/0184391 A1 | 8/2006 | Barre et al. |
| 2006/0259363 A1 | 11/2006 | Jhetam |
| 2007/0005402 A1 | 1/2007 | Kennedy et al. |
| 2007/0050209 A1 | 3/2007 | Yered |
| 2007/0136100 A1 | 6/2007 | Daugherty et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2008/0078828 A1* | 4/2008 | Helmin et al. .......... 235/375 |

FOREIGN PATENT DOCUMENTS

| | | |
|---|---|---|
| WO | 9503569 | 2/1995 |
| WO | 0039737 | 7/2000 |
| WO | 2007025295 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

* cited by examiner

SYSTEMS AND METHODS FOR ENHANCED MIN/MAX EDIT FOR DRUG CLAIM SUBMISSION VERIFICATION

FIELD OF THE INVENTION

Aspects of the invention relate generally to prescription drugs, medications, over-the-counter drugs, or other medical devices (collectively referred to herein as "drugs"), and more particularly, to systems and methods for verifying drug claims submitted by pharmacies.

BACKGROUND OF THE INVENTION

In filling prescriptions for customers, pharmacies may also submit corresponding claims to third-party payors for reimbursement. However, the process of submitting these claims is oftentimes error-prone. For example, pharmacy employees may inadvertently specify the incorrect quantity, package size, and/or days supply when submitting claims to the third-party payors. Accordingly, these incorrect claims can result in either overbillings or underbillings to the third-party payors. Furthermore, these incorrect claims may result in additional audits of claims submitted by a pharmacy. Audits are generally disruptive, time-consuming, and costly to pharmacies. Accordingly, there is a need in the industry to improve the accuracy of claims submitted by pharmacies, thereby preventing or minimizing audits of those claims.

SUMMARY OF THE INVENTION

According to an embodiment of the invention, there is a computer-implemented method. The method includes storing a Multiple Package Edit (MPE) table that includes drug package size information, storing an audit table that includes drug dose information, and storing a user table that includes pharmacy-supplied drug information. The method further includes receiving a first claim submission from a pharmacy computer, where the first claim submission includes at least one identifier, a quantity, and days supply for a requested drug, determining that the first claim submission includes an error in at least one of the quantity and days supply based upon information obtained from at least one of the user table, the MPE table, and the audit table, and messaging the pharmacy computer with an indication of the determined error.

According to another embodiment of the invention, there is a system. The system includes a memory for storing computer-executable instructions, a Multiple Package Edit (MPE) table that includes drug package size information, an audit table that includes drug dose information, and a user table that includes pharmacy-supplied drug information. The system further includes a processor in communication with the memory, where the processor is operative to execute the computer-executable instructions to receive a first claim submission from a pharmacy computer, where the first claim submission includes at least one identifier, a quantity, and days supply for a requested drug, determine that the first claim submission includes an error in at least one of the quantity and days supply based upon information obtained from at least one of the user table, the MPE table, and the audit table, and message the pharmacy computer with an indication of the determined error.

According to yet another embodiment of the invention, there is another system. The system includes a memory for storing computer-executable instructions, a Multiple Package Edit (MPE) table that includes drug package size information, an audit table that includes drug dose information, and a user table that includes pharmacy-supplied drug information. The system further includes means for receiving a first claim submission from a pharmacy computer, where the first claim submission includes at least one identifier, a quantity, and days supply for a requested drug, means for determining that the first claim submission includes an error in at least one of the quantity and days supply based upon information obtained from at least one of the user table, the MPE table, and the audit table, and means for messaging the pharmacy computer with an indication of the determined error.

BRIEF DESCRIPTION OF THE DRAWINGS

Reference will now be made to the accompanying drawings, which are not necessarily drawn to scale, and wherein:

FIG. 5 illustrates an exemplary user interface for adding/modifying/deleting rows in the User Table, according to an embodiment of the invention.

FIG. 7 illustrates an exemplary user interface for adding/modifying/deleting rows in the Audit Table, according to an embodiment of the invention.

DETAILED DESCRIPTION

Figure 1:
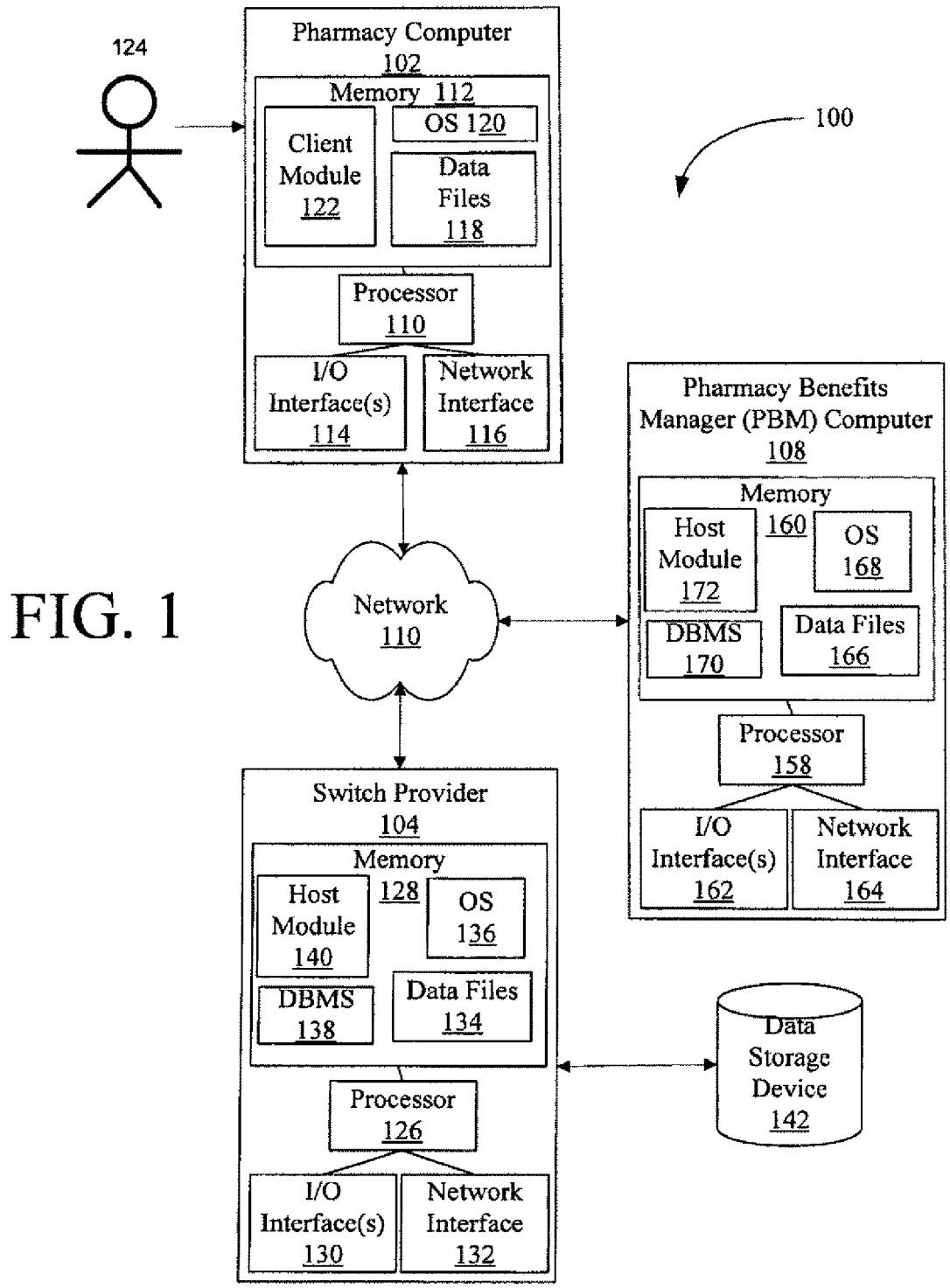
FIG. 1 illustrates an exemplary system that allows a switch provider to inform a pharmacy of issues regarding the submitted quantity, package sizes, and/or days supply associated with a drug claim submission, according to an embodiment of the invention.

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention are described below with reference to block diagrams and flowchart illustrations of systems, methods, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer such as a switch, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data-processing apparatus to cause a series of operational elements or steps to be performed on the computer or other programmable apparatus to produce a computer-implemented process such that the instructions that execute on the computer or other programmable apparatus provide elements or steps for implementing the functions specified in the flowchart block or blocks.

Accordingly, blocks of the block diagrams and flowchart illustrations may support combinations of means for performing the specified functions, combinations of elements or steps for performing the specified functions, and program instruction means for performing the specified Functions. It will also be understood that each block of the block diagrams and flowchart illustrations, and combinations of blocks in the block diagrams and flowchart illustrations, can be implemented by special purpose hardware-based computer systems that perform the specified functions, elements or steps, or combinations of special purpose hardware and computer instructions.

Embodiments of the invention can provide means and mechanisms by which a switch provider can message or otherwise inform a pharmacy of issues regarding a drug claims submission, including errors in the quantity, package size, and/or days supply. By informing the pharmacy of such issues, the pharmacy can correct the claim submission before a third-party payor, such a pharmacy benefits manager (PBM), receives an incorrect or inaccurate submission. Accordingly, reducing the number of erroneous claim submissions may prevent or otherwise reduce the number of overbillings and underbillings by the pharmacy. Overbillings may result in third-party audits and adjustments to reimbursements, while underbillings may reduce profits by the pharmacy. An exemplary system that allows a switch provider to verify a claim submission, including one or more of days supply, package size, and quantity of a drug, will now be described with respect to FIG. 1.

System Overview. FIG. 1 illustrates an exemplary system 100 in which a switch provider can inform a pharmacy of issues regarding potential issues or errors in a claim submission, including, but not limited to, the submitted quantity, package size, and/or days supply associated with a drug claim submission. In particular, the system 100 includes at least one pharmacy computer 102, at least one switch provider 104, and a pharmacy benefits manager (PBM) computer 108 or other third-party payor. The pharmacy computer 102, switch provider 104, and PBM computer 108 are each configured for accessing and reading associated computer-readable media having stored thereon data and/or computer-executable instructions for implementing the various methods described herein. Generally, the pharmacy computer 102 submits claims to the PBM computer 108 via the switch provider 104. The PBM computer 108 may determine benefits, coverage, and/or extent of coverage for one or more claims submitted by the pharmacy computer 102. The PBM may include any third-party payors such as insurance companies, Medicare, and the like.

Generally, network devices and systems, including the one or more pharmacy computers 102, switch providers 104, and PBM computers 108 have hardware and/or software for transmitting and receiving data and/or computer-executable instructions over a communications link and a memory for storing data and/or computer-executable instructions. These network devices and systems may also include a processor for processing data and executing computer-executable instructions, as well as other internal and peripheral components that are well-known in the art. As used herein, the term "computer-readable medium" describes any form of memory or a propagated signal transmission medium. Propagated signals representing data and computer-executable instructions are transferred between network devices and systems.

Still referring to FIG. 1, the pharmacy computer 102 is in communication with the switch provider 104 via a network 110. As described below, the network 110 can be provided in various configurations of one or more private and/or public networks, including the Internet. Likewise, the switch provider 104 may also be in communication with a PBM computer 108 via the network 110. The pharmacy computer 102, switch provider 104, PBM computer 108, and network 110 will now be discussed in further detail below.

First, the pharmacy computer 102 may be any processor-driven device, such as a personal computer, laptop computer, handheld computer, and the like. In addition to having a processor 110, the pharmacy computer 102 may further include a memory 112, input/output ("I/O") interface(s) 114, and a network interface 116. The memory 112 may store data files 118 and various program modules, such as an operating system ("OS") 120 and a client module 122. The client module 122 may be an Internet browser or other software, including a dedicated program, for interacting with the switch provider 104 and/or PBM computer 108. For example, a user such as a pharmacist or other pharmacy employee, may utilize the client module 122 in preparing and submitting a drug claim to the PBM computer 108 via the switch provider 104. The pharmacy computer 102 may also utilize the client module 122 to retrieve or otherwise receive data from the switch provider 104, including messages or other indications associated with a submitted drug claim. In addition, the I/O interface(s) 114 can facilitate communication between the processor 110 and various I/O devices, such as a keyboard, mouse, printer, microphone, speaker, monitor, bar code readers/scanners, RFID readers, and the like. The network interface 116 can take any of a number of forms, such as a network interface card, a modem, a wireless network card, and other communications devices. These and other components of the pharmacy computer 102 will be apparent to those of ordinary skill in the art and are therefore not discussed in more detail herein.

Second, the switch provider 104 can include any processor-driven device that is configured for verifying claims submitted from the pharmacy computer 102 (e.g., including verifying days supply, package size, and/or quantity of a drug). The switch provider 104 can include a processor 126, a memory 128, input/output ("I/O") interface(s) 130, and a network interface 132. The memory 128 can store data files 134 and various program modules, such as an operating system ("OS") 136, a database management system ("DBMS") 138, and a host module 140.

According to an embodiment of the invention, the data files 134 can store routing tables for determining which PBM computer 108 to route the claims submissions received from the pharmacy computers 102. For example, these routing tables may determine that claim submissions having certain destination identification numbers are to be routed to particular PBM computers 108. The data files 134 can also store one or more tables, computer-executable instructions, parameters, and other data, as described herein, to be used for verifying claim submissions, including verifying the days supply, package size, and/or quantity of a claim submission. For example, these tables stored as part of data files 134 can include one or more User Tables, Multiple Package Edit (MPE) tables, and Audit Tables, as described herein. The User Table can allow a pharmacy to add new drugs or information for existing drugs that may not be available on the MPE Tables and/or Audit Tables. The User Table may be used by the switch provider 104 to verify claim submissions, including package sizes, multiples, minimum quantity, maximum quantity, minimum days supply, and maximum days supply, as described in further detail herein. Likewise, the MPE Table may allow a switch provider 104 to verify that a submitted quantity is a multiple of the unit-of-use package size and compare the submitted quantity to a database, perhaps in data storage device 142, of items identified as being a unit-of-use package, such as oral contraceptives, oral and nasal inhalers, steroidal and antibiotic dose packs, kits, pre-filled syringes, and opthalmic solutions. Similarly, the Audit Table may be used by the switch provider 104 to verify the daily dose based upon the quantity dispensed and the days supply. As described below, the user, MPE, and Audit Tables may be used in a hierarchical or a prioritized order, according to an embodiment of the invention. In addition, while these user, MPE, and Audit Tables may be referred to as "tables," it will be appreciated that they may be stored in a variety of formats, including databases, files (e.g., CSV files), and the like. Thus, according to an embodiment of the invention, the User Table, the MPE Table, and Audit Tables may be provided in a single, separate, or distributed database.

Still referring to the switch provider 104, the host module 140 initiates, receives, processes, verifies, and responds to requests from the respective client module 122 of pharmacy computer 102, and further initiates, receives, processes, and responds to requests from the respective host modules 172 of the PBM computer 108. The switch provider 104 can include additional program modules for performing other pre-processing or post-processing methods, including the claim verification methods described herein. Those of ordinary skill in the art will appreciate that the switch provider 104 may include alternate and/or additional components, hardware or software without departing from embodiments of the invention.

As illustrated in FIG. 1, the switch provider 104 may include or be in communication with at least one data storage device 142 or database. If the switch provider 104 includes the data storage device 142, then the data storage device 142 could also be part of the memory 128. Furthermore, data stored in the memory 128 could alternatively be stored within the storage device 142. Accordingly, the data storage device 142 and/or memory 128 may store, for example, one or more tables, computer-executable instructions, parameters, and other data, including information for one or more drugs, as described herein, to be used for claim submission verification (e.g., days supply, package size, and/or quantity of one or more drugs). Although a single data storage device 142 is referred to herein for simplicity, those skilled in the art will appreciate that multiple physical and/or logical data storage devices or databases may be used to store the above mentioned data. For security and performance purposes, the switch provider 104 may have a dedicated connection to the data storage device 142. However, the switch provider 104 may also communicate with the data storage device 142 via a network 110, as shown. In other embodiments of the invention, the switch provider 104 may include the data storage device 142 locally. The switch provider 104 may also otherwise be part of a distributed or redundant database management system ("DBMS").

Third, the PBM computer 108 may include any processor-driven device that is configured for receiving, processing, and fulfilling requests from the switch provider 104 related to the pharmacy and benefits transactions. The PBM computer 108 may therefore include a processor 158, a memory 160, input/output ("I/O") interface(s) 162, and a network interface 164. The memory 160 may store data files 166 and various program modules, such as an operating system ("OS") 168, a database management system ("DBMS") 170, and the host module 172. The host module 172 initiates, receives, processes, and responds to requests from host module 140 of the switch provider 104, as described above. The PBM computer 108 may include additional program modules for performing other pre-processing or post-processing methods described herein. Those of ordinary skill in the art will appreciate that the PBM computer 108 may include alternate and/or additional components, hardware or software without departing from embodiments of the invention.

Finally, the network 110 may include any telecommunication and/or data network, whether public, private, or a combination thereof, including a local area network (LAN), a metropolitan area network (MAN), a wide area network (WAN), an intranet, an internet, the Internet, intermediate hand-held data transfer devices, and/or any combination thereof and may be wired and/or wireless. The network I/O may also allow for real-time, off-line, and/or batch transactions to be transmitted between the pharmacy computer 102 and the switch provider 104. Due to network connectivity, various methodologies as described herein may be practiced in the context of distributed computing environments. Although the pharmacy computer 102 is shown for simplicity as being in communication with the switch provider 104 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices of the invention. According to an embodiment of the invention, the network 110 may include a network including, or similar, to RelayHealth's Intelligent Network.

Those of ordinary skill in the art will appreciate that the system 100 shown in and described with respect to FIG. 1 is provided by way of example only. Numerous other operating environments, system architectures, and device configurations are possible. Accordingly, the invention should not be construed as being limited to any particular operating environment, system architecture, or device configuration.

As discussed above with respect to FIG. 1, embodiments of the invention may provide means and mechanisms, including "edits", by which a switch provider 104 can review a claim submission and message or otherwise inform a pharmacy 102 of issues or errors regarding the submitted claim. According to an embodiment of the invention, these issues or errors may be associated with the quantity, package size, and/or days supply specified in the drug claim submission. The operation of embodiments of the invention will now be described below with reference to FIG. 2.

Figure 2:
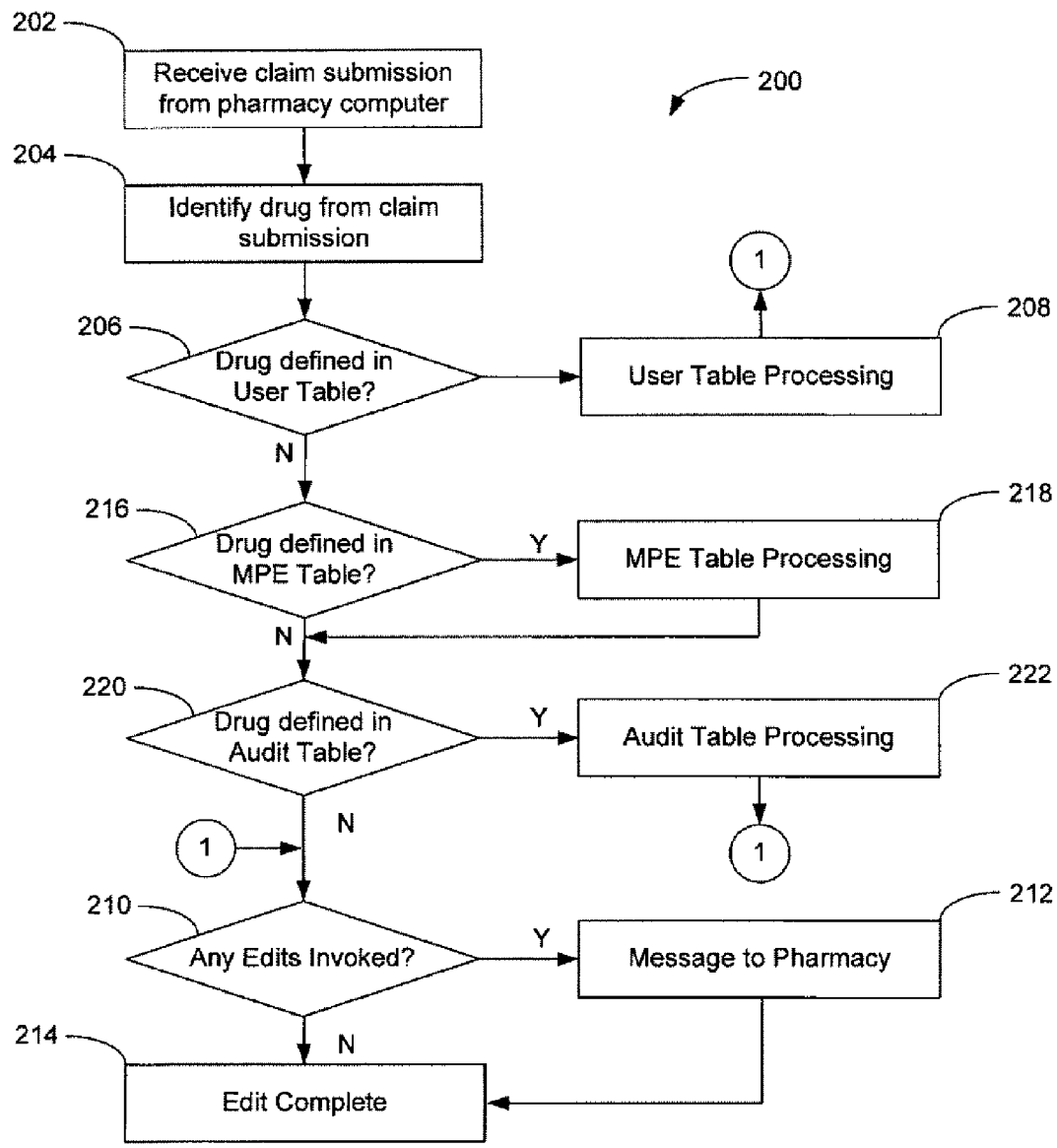
FIG. 2 illustrates a flow diagram of an edit method, according to an exemplary embodiment of the invention.

Operational Overview. FIG. 2 provides a an overview of an exemplary edit method 200 for verifying a claim submission received from a pharmacy computer 102. According to an embodiment of the invention, the method 200 allows a switch provider 104 to verify one or more of days supply, package size, quantity, and doses per day of a drug in a claim submission provided by a pharmacy computer 102. In particular, in step 202, the switch provider 104 initially receives a claim submission from the pharmacy computer 102. In step 104, the switch provider 104 examines the claim submission to determine the drug specified or otherwise requested (e.g., by National Drug Code (NDC), Generic Code Sequence (GCN) number, name of drug, etc.) submission. In step 206, the switch provider 104 may determine whether the User Table is enabled. Assuming the User Table is enabled, the switch provider 104 determines whether the requested drug has been defined in the User Table by a pharmacy or representative thereof (e.g., a sponsor). For example, according to an embodiment of the invention, the switch provider 104 may determine whether the User Table includes one or more of the following pharmacy-supplied information: drug identifier (e.g., NDC, GCN number, name of drug, etc.), user-defined package size or First Data Bank (FDB) package size information, days supply information (e.g., minimum days supply, maximum days supply), and quantity information (minimum quantity, maximum quantity). In accordance with an embodiment of the invention, Table I below provides a description of some illustrative fields of the User Table. It will be appreciated that other fields may be available in the User Table without departing from embodiments of the invention, including a maximum or minimum doses per day.

TABLE 1

| Field | Description |
| --- | --- |
| NDC | Drug NDC# |
| BIN | Select if only screening on a specific Banking Identification Number (BIN) |
| BIN Description | BIN name |
| Verify FDB Package Size OR | Select to verify the submitted quantity is equal to FDB package size. |
| User Package Size | Enter quantity if customer of service provider (e.g., a pharmacy) (referred to as a "sponsor") wants a quantity different than FDB package size. |
| Check Multiples | Verifies the minimum or maximum daily doses on multiple quantities. Used with Quantity and Days Supply. Example: inhaler package size is 15 gm Pharmacy submits quantity of 30 If min and/or max quantity and days supply fields are populated in the User Table, then the edit will calculate appropriate doses per day based on qty divided by days supply to yield the doses per day. |
| Minimum Quantity (Optional) | This is minimum quantity that the sponsor wishes for the pharmacy to fill. Example: birth control pills usually come in a quantity of 28. If 28 were populated in the min qty, and the pharmacy submits any of 1–27 for the quantity, then "Min Quantity is 28" would message back to the pharmacy. This can also be accomplished by checking the "Verify FDB package size" option. |
| Maximum Quantity | This is the maximum quantity that the sponsor wishes the pharmacy to fill. Example: If a state law prohibits a pharmacy from dispensing a maximum quantity of a controlled substance, the maximum quantity filed could be utilized. For instance, Oxycotin maximum quantity is 120 in some states for a 60 day supply. Maximum Quantity can be selected to be large enough to cover all scenarios so that dispensing is not limited unnecessarily. According to an embodiment of the invention, a one year supply for the maximum quantity may be acceptable. |
| Minimum Days Supply (Optional) | Minimum days supply that the sponsor wishes the pharmacy to fill. |
| Maximum Days Supply | This is the maximum days supply that the sponsor wishes the pharmacy to fill. In the example for the max quantity field, the max qty was 120 but the maximum days supply was 60. Maximum Days Supply can be selected to be large enough to cover all scenarios so that dispensing is not limited unnecessarily. According to an embodiment of the invention, a one year supply for the maximum quantity may be acceptable. |

If step 206 determines that the User Table is enabled and that the requested drug has been defined in the User Table, then processing continues with step 208. In step 208, the User Table information for the requested drug is used to process the information in the claim submission to determine whether any errors exist in submitted days supply, package size, quantity, and/or doses per day. In particular, the submitted quantity and days supply in the claim submission can be checked for errors against one or more of the following information stored or otherwise defined in the User Table for the drug: the package size, the minimum quantity, the maximum quantity, the minimum days supply, maximum days supply. For example, a User Table edit can be invoked (i.e., indicating an error or potential error) if the submitted quantity in the claim does not match the FDB package size stored in the User Table, or a multiple thereof. Alternatively, a User Table edit can be invoked if the submitted quantity does not match pharmacy-supplied package size information in the User Table, or a multiple thereof. Likewise, a User Table edit can be invoked if the submitted quantity exceeds the bounds of either the minimum quantity or the maximum quantity. Similarly, a User Table edit can be invoked if the submitted days supply exceeds the bounds of either the minimum days supply or the maximum days supply. Furthermore, the doses per day (i.e., submitted quantity/submitted days supply) can be compared to a calculated maximum or minimum doses per day (i.e., max quantity/max days supply or min quantity/min days supply), according to an embodiment of the invention. Alternatively, the minimum or maximum doses per day be directly available for retrieval from the User Table.

Following step 208, processing continues with step 210. Step 210 determines whether any edits were invoked (in this case, based upon the User Table, but generally based upon any of the User Table, MPE Table, and Audit Table). If any edits were invoked in step 208, then a message will be sent to the pharmacy computer 102, as provided in step 212. The claim may also be rejected as well in some embodiments of the invention. According to an embodiment of the invention, the message to the pharmacy computer 102 can identify the error in the submitted package size, quantity, days supply, and/or doses per day (i.e., quantity/days supply). Table II below illustrates sample messages that can be sent to the pharmacy computer 102 based upon certain information (i.e., populated fields) of the User Table. It will be appreciated that the messages in Table II are illustrative and can be modified variously without departing from embodiments of the invention.

lar, the submitted quantity can be checked for errors in the FDB package size. If any error is determined in the submitted quantity, then an MPE Table edit can be invoked. For example, several examples of MPE Table edits that can be invoked are provided as follows:

If a pharmacy dispenses a Combivent Inhaler (which FDB package size is 15 gm in the MPE Table), and "1" is entered as the quantity in the claim submission, then an MPE Table edit will be invoked.

If the FDB pack size is 10 and the pharmacy submits anything that is not a multiple of 10, then an MPE Table edit will be invoked.

Following step 218, processing proceeds with step 220. Likewise, processing also proceeds with step 220 if the MPE Table is not enabled or if the requested drug is not defined in the MPE Table.

Step 220 may determine whether the Audit Table is enabled. If the Audit Table is enabled, then step 220 may further determine whether the requested drug has been defined in the Audit Table. For example, the switch provider 104 determines whether the Audit Table includes one or more of the following information: GCN Sequence, Form Strength, Maximum Allowable Daily Dose, Form, NDC, and Package Size. If step 220 determines that the Audit Table is enabled and that the requested drug is defined in the Audit Table is enabled, then processing proceeds with step 222.

In step 222, the Audit Table information for the requested drug is used to process information in the claim submission to determine whether any issues or errors exist in the submitted

TABLE II

| Message | Populated User Table Fields |
|---|---|
| Min Quantity is [Min Qty] | NDC and Min Quantity |
| Max Quantity is [Max Qty] | NDC and Max Quantity |
| Min Days Supply is [Min Days Supply] | NDC and Min Days Supply |
| Max Days Supply is [Max Days Supply] | NDC and Max Days Supply |
| Doses per Day [Calculated Doses] [Drug Form Code] too low | NDC Check Multiples is checked. Min Quantity, and Min Days Supply are populated. Note: Use the formula Min Quantity/Min Days Supply to verify that the Minimum Allowable Doses Per Day is correct. |
| Doses per Day [Calculated Doses] [Drug Form Code] exceeds allowable [Max Dose Allowed] [Drug Form Code] | NDC Check Multiples is checked. Max Quantity and Max Days Supply are populated. Note: Use the formula Max Quantity/Max Days Supply to verify that the Maximum Allowable Doses Per Day is correct. |
| Dispense in Multiples of [Package Size] only | NDC and verify FDB Package Size is checked or User Package Size is populated. |

Referring back to step 206, the User Table may not be enabled and/or the requested drug may not be defined in the User Table. In this case, processing continues with step 216. Step 216 may determine whether the MPE Table is enabled. If the MPE Table is enabled, then step 216 may further determine whether the requested drug has been defined in the MPE Table. For example, the switch provider 104 determines whether the MPE Table includes one or more of the following information: NDC and FDB Package Size. If step 216 determines that the MPE Table is enabled and that the requested drug has been defined in the User Table, then processing continues with step 218.

In step 218, the MPE Table information for the requested drug is used to process the claim submission to determine whether any errors exist in the submitted quantity. In particucombination of quantity and days supply. In particular, according to an embodiment of the invention, the submitted quantity can be divided by the submitted days supply to determine a calculated daily dose. The calculated daily dose can then be compared to the maximum daily dose specified for the drug in the Audit Table. If the calculated daily dose exceeds the maximum daily dose, then an Audit Table edit can be invoked. Several examples of Audit Table edits that can be invoked are provided as follows:

If a pharmacy dispenses TRAVATAN opth sol with a quantity of 5 ml for a 10 day supply, then an Audit Table edit will be invoked because according to the package insert, the maximum allowable daily dose is 0.1000 ml and the calculated daily dose of 0.5000 ml (i.e., qty/ds=5 ml/10 days=0.5000 ml) is too high.

If a pharmacy submits an NDC# for an inhaler that is on the Audit Table with quantity of 15 and days supply of 5 (equals 3 doses per day derived by dividing the submitted quantity by the submitted days supply) and the Audit Table maximum daily dose is 2, then an Audit Table edit will be invoked.

Following step 222, processing proceeds with step 210. Processing likewise continues with step 210 where the Audit Table was not enabled or where the drug was not defined in the Audit Table. Step 210 determines whether any edits have been invoked based upon one or more of (i) User Table Processing in step 208, (ii) MPE Table processing in step 218, and (iii) Audit Table processing in step 222. If any edits have been invoked, then a message will be sent to the pharmacy computer 102, as provided in step 212. According to an embodiment of the invention, the message to the pharmacy computer 102 can identify the error in the submitted package size, quantity, days supply, and/or doses per day (i.e., quantity/days supply). For example, an error based upon information in the MPE table may be provided as follows: "Dispense in Multiples of [Package Size] Only." Likewise, an error based upon information in the Audit Table may be provided as follows: "Doses per Day [Calculated Doses] [Drug Form Code] exceeds allowable." It will be appreciated that these sample messages are provided by way of example only. Additionally, if any edits have been invoked, then the service provider 104 can reject the claim according to an embodiment of the invention. On the other hand, if no edits have been invoked (based upon any of the User Table Processing in step 208, the MPE Table processing in step 218, and the Audit Table processing in step 222), then the edit is complete in step 214. The switch provider 104 can then route the claims submission to the PBM computer 108 for benefits determination and processing.

It will be appreciated that once the pharmacy computer 102 has received the message indicating an error in the submitted package size, quantity, days supply, and/or doses per day, the pharmacy 102 can submit a subsequent claim to the switch provider 104 that corrects the error. In such a case, the switch provider 104 will utilize one or more of the User Table, MPE Table, and/or Audit Table, as described above, to determine any errors in the subsequent claim submission. Assuming that no edits have been invoked (based upon any of the User Table Processing in step 208, the MPE Table processing in step 218, and the Audit Table processing in step 222), then the edit is complete, and the switch provider 104 can then route the claims submission to the PBM computer 108 for benefits determination and processing.

It will be appreciated that variations to the edit method 200 in FIG. 2 are available in accordance with other embodiments of the invention. For example, according to an embodiment of the invention, the service provider 104 can message the pharmacy computer 102, but not reject the claim. Thus, the claim may still be routed to the PBM computer 108 for benefits determination and processing. In addition, it will be appreciated that instead of rejecting the claim and/or messaging the pharmacy computer 102, the switch provider can simply record the determined error in its memory for later retrieval and review. In such a case, the switch provider 104 may also route the claim to the PBM computer 108 for benefits determination and processing.

According to another embodiment of the invention, one or more of the MPE Table and the Audit Table may include exclusion lists for one or more drugs. The exclusion list may be specified by one or more pharmacies to be used in instances where drugs need to be dispensed in a specific way, and require overriding of an edit such as edit method 200.

Figure 3:
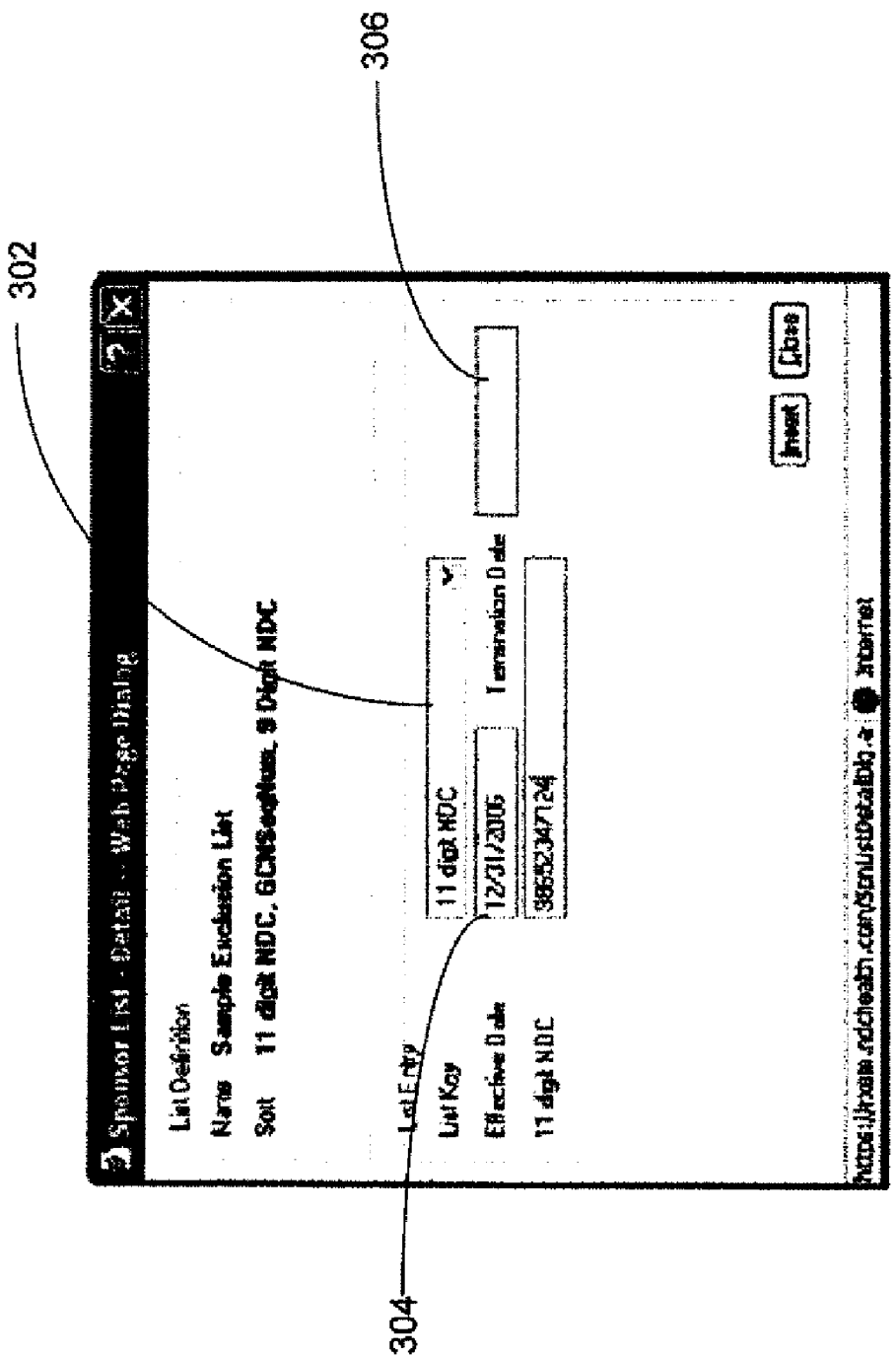
FIG. 3 provides an exemplary user interface for adding one or more drugs to an exclusion list, according to an embodiment of the invention.

FIG. 3 illustrates a user interface by which a pharmacy can identify one or more drugs to be included an exclusion list. As illustrated in FIG. 3, the drug can be identified (e.g., the List Key 302) by an 11 digit NDC, a GCN Sequence Number, a 9 digit NDC, or another identifier. In addition, an effective date 304 or termination date 306 can be specified for a drug in the exclusion list. The effect date 304 and termination date 306 specify the time periods that a drug will be excluded from an edit. If no termination date 306 is specified, then the specified drug may be excluded from the edit until the exclusion list is otherwise modified.

According to another embodiment of the invention, the Audit Table processing in step 222 may be performed prior to the MPE Table processing in step 218. According to yet another embodiment of the invention, the processing may initially assess whether the drug is defined in the User Table, Audit Table, and MPE Table prior to determining which table(s) will actually be utilized for processing. Alternatively, all three of the User Table, Audit Table, and MPE Table may be used for verifying the claim submission.

According to another embodiment of the invention, there may be variations in the prioritizations and selections between or among the User Table, Audit Table, and MPE Table. For example, MPE Table and Audit processing may be preferred over User Table processing. Accordingly, in this embodiment, the User Table will be utilized only if the drug has not been defined by the MPE Table and/or Audit table. In yet further embodiments of the invention, two or more of the user, MPE, and Audit tables may be combined into a single table or database, either during runtime or prior to runtime.

An Exemplary Embodiment. The exemplary edit method 200 described generally with respect to FIG. 2 can be implemented in various ways without departing from embodiments of the invention. Indeed, another embodiment of an edit method 400 is illustrated with respect to FIG. 4.

Figure 4:
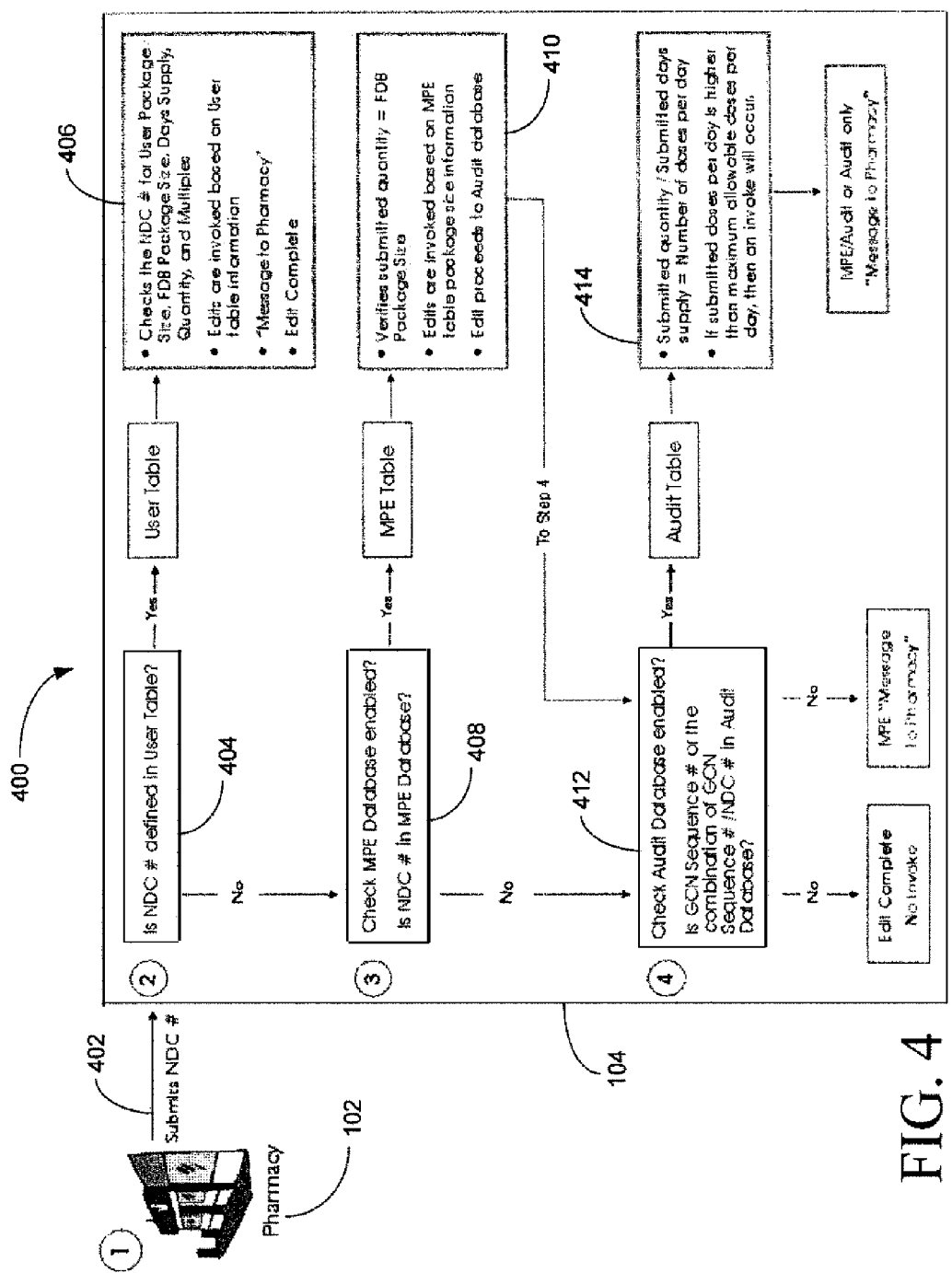
FIG. 4 provides an illustrative embodiment of an edit method by which a switch provider can verify one or more of days supply, package size, and quantity of a drug in a claim submission by a pharmacy, according to an exemplary embodiment of the invention.

Referring to FIG. 4, in step 402, a pharmacy computer 102 submits a claim to the switch provider 104. The claim submission may include sufficient information to identify the requested drug, which may include the National Drug Code (NDC) number or other drug identifier, according to an embodiment of the invention. The claim submission may also indicate the quantity of the drug and/or days supply of the drug.

In step 404, the switch provider 104 determines whether the NDC number or other drug identifier has been defined in the User Table. If yes, then processing proceeds to step 406. As illustrated in step 406, the User Table is checked for one or more of the following information: FDB package size, user package size, days supply, quantity, and multiples. Based upon the User Table information, the submitted quantity and/or days supply are verified. For example, if the maximum quantity and maximum days supply portion of the User Table is populated, the maximum quantity field may be divided by the maximum days supply field to calculate maximum allowable daily doses. The submitted quantity is divided by the submitted days supply (by the pharmacy) to obtain a submitted doses per day. If the submitted doses per day is not within the parameters set in the User Table, then an edit will be invoked and a message will be provided to the pharmacy computer 102. Accordingly, if an issue or error arises with the submitted quantity and/or days supply, then the switch provider 104 may invoke an edit and provide a message reporting or indicating such issues to the pharmacy computer 102. If no issues were detected (i.e., no edits were invoked), then the switch provider 104 may route the claim submission to the appropriate PBM computer 108 for further processing.

On the other hand, if in step 404, the switch provider 104 determines that the NDC number or other drug identifier has not been defined in the User Table, then processing proceeds to step 408. Step 408 checks to determine whether the MPE database has been enabled and if so, whether the NDC number or other drug has been defined in the MPE database. If yes, then processing proceeds to step 410. Step 410 verifies that the submitted quantity equals or is a multiple of the FDB package size. If an issue arises with the submitted quantity not equaling or being a multiple of the FDB package size, then an edit may be invoked, and the edit may proceed to step 412. Processing may also flow to step 412 if step 408 determines that the MPE database has not been enabled and/or the NDC number or other drug identifier is not in the MPE database.

Step 412 determines whether the audit database has been enabled. If so, then step 412 also determines whether the Generic Code Number (GCN) Sequence Number or the combination of the GCN Sequence Number/NDC# is in the audit database. If not, then the edit is complete and a message will be provided to the pharmacy computer 102. The message may indicate that either no edit was invoked or that an MPE-based invoke occurred, as previously indicated in step 410. If no issues were detected (i.e., no edit was invoked), then the switch provider 104 may continue processing of the claim submission by routing it to the appropriate PBM computer 108.

On the other hand, in step 412, if the GCN Sequence Number or the combination of the GCN Sequence Number/NDC# is in the audit database, then processing continues with step 414. In step 414, the submitted quantity is divided by the submitted days supply to obtain a submitted number of doses per day. If the submitted doses per day is higher than the maximum allowable doses per day, then an edit will be invoked, and a message will be provided to the pharmacy computer 102 indicating an invoke based upon the MPE & Audit tables or simply the Audit table. If the submitted doses per day is not higher than the maximum allowable dose, then a message will be provided to the pharmacy computer 102 indicating either no invoke or an invoke based upon the MPE Table. If no issues were detected, then the switch provider 104 may route the claim submission to the appropriate PBM computer 108 for further processing.

Figure 5:
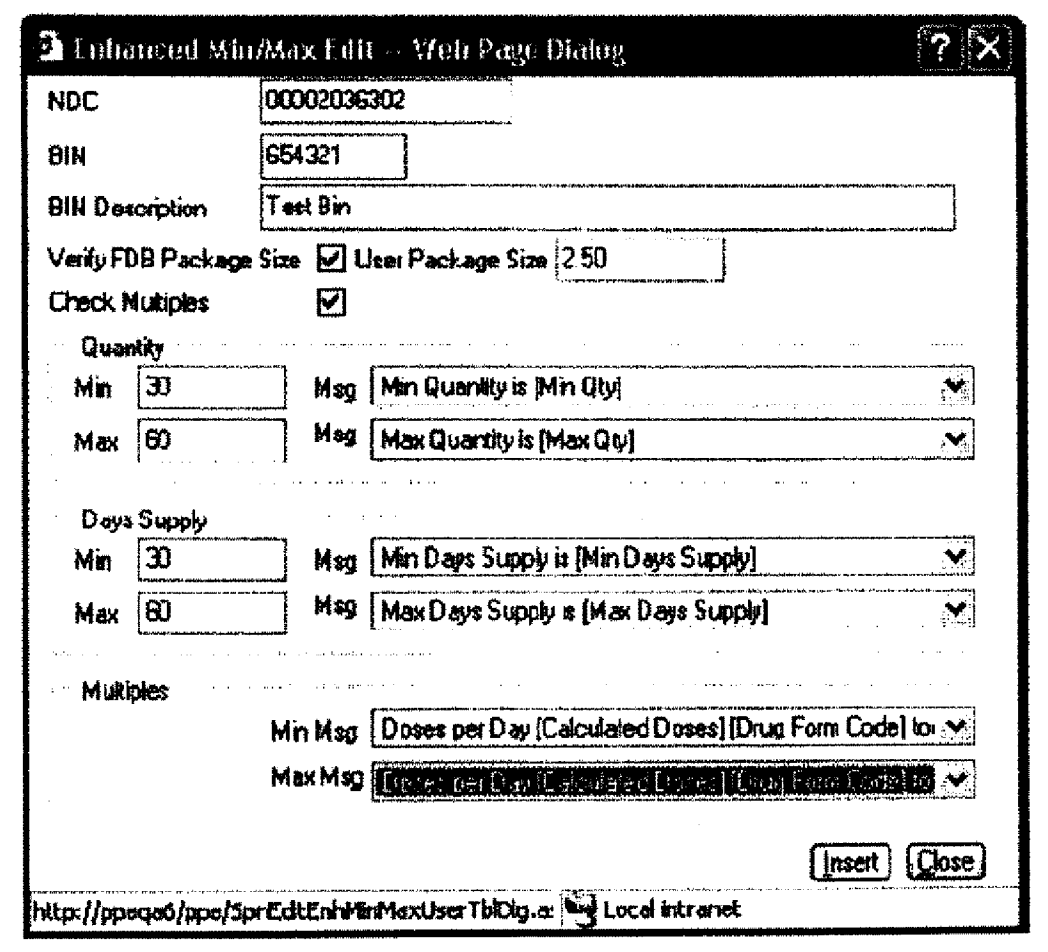

User Table. The User Table discussed FIGS. 2 and 4 will now be described in further detail. In particular, FIG. 5 illustrates an exemplary user interface for adding/modifying/deleting rows in the User Table. As shown in FIG. 5, User Table information may include one or more of the following fields in Table III.

It will be appreciated that other examples of the User Table are available without departing from embodiments of the invention. According to an embodiment, the User Table may be stored on the switch provider 104, but set up and maintained by the pharmacy computer 102. The pharmacy computer 102 can then access and update the User Table over network 110. Alternatively, the pharmacy computer 102 can provide instructions to the switch provider 104 to update the User Table using email, postal mail, facsimile and the like.

Figure 6:
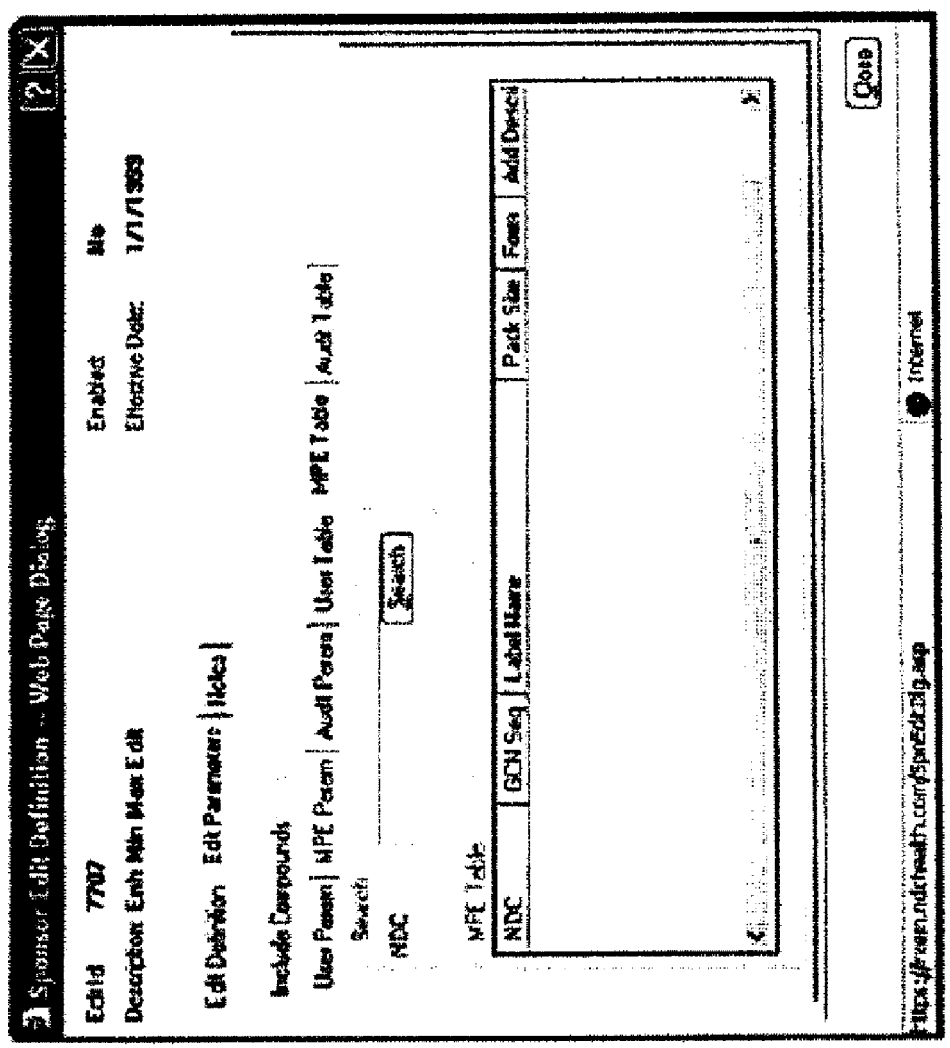
FIG. 6 illustrates an exemplary user interface for adding/modifying/deleting rows in the MPE Table, according to an embodiment of the invention.

MPE Table. The MPE Table or database discussed with respect to FIGS. 2 and 3 will now be described in further detail. The MPE Table may be used for verification that the quantity dispensed matches or is a multiple the FDB package size. For example, if a pharmacy 102 dispenses a Combivent Inhaler (which FDB pkg size is 15 gm)—and they enter "1" as the quantity, then an edit will occur because Combivent is on the MPE Table and a qty of "1" is not the FDB package size. According to an embodiment of the invention, the fields of the MPE Table can include the NDC, GCN Sequence, Label Name, Package Size, Form, and Add Descriptor. It will be appreciated that other examples of the MPE Table are available without departing from embodiments of the invention. According to an embodiment of the invention, the MPE Table may be maintained and updated by the switch provider 104 or an entity such as RelayHealth. For example, the MPE Table may be maintained via a monthly update by RelayHealth. Other maintenance or update periods besides monthly are available without departing from embodiments of the invention. FIG. 6 illustrates an exemplary user interface for adding/modifying/deleting rows in the MPE Table, according to an embodiment of the invention.

Audit Table. The Audit Table or database discussed with respect to FIGS. 2 and 4 will now be discussed in further detail. Generally, the Audit table may be used by the switch provider 104 to help prevent third-party audits, rejects, or inappropriate payments cause by an atypical daily dose being dispensed. Information from the Audit table may be used to calculate daily doses based on quantity dispensed and days supply.

The fields of the Audit Table may include GCN sequence, form strength, max allowable daily dose, form, NDC, and Package Size. It will also be appreciated that other fields of the Audit Table are available without departing from embodiments of the invention. According to an embodiment of the invention, the Audit Table may be maintained and updated by the switch provider 104 or an entity such as RelayHealth. For

TABLE III

Figure 7:
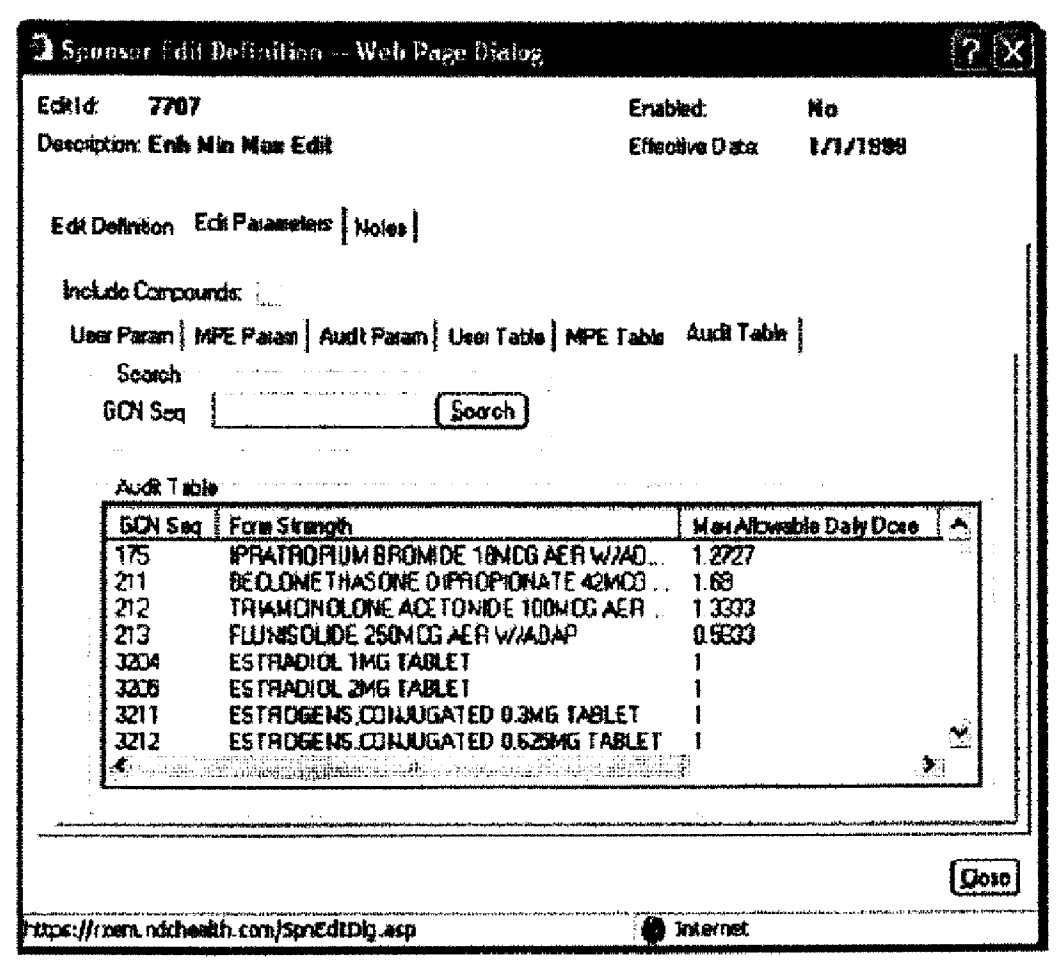

| Field | Description |
| --- | --- |
| NDC | Drug NDC # |
| BIN | Select if only screening on a specific BIN# |
| BIN Description | BIN name |
| Verify FDB Package Size OR | Select to verify the submitted quantity is equal to or a multiple of the FDB Package size. |
| User Package Size | Enter quantity if customer wants a quantity different than FDB package size. |
| Check Multiples | Verifies the minimum or maximum daily doses on multiple quantities. Used with Quantity and Days Supply |
| Minimum Quantity (Optional) | Minimum quantity that the customer wishes for the pharmacy to fill |
| Maximum Quantity | Maximum quantity that the customer wishes for the pharmacy to fill |
| Minimum Days Supply (Optional) | This is the minimum days supply that the sponsor wishes the pharmacy to fill |
| Maximum Days Supply | This is the maximum days supply that the sponsor wishes the pharmacy to fill | example, the Audit Table may be maintained via a monthly update by RelayHealth. Other maintenance or update periods besides monthly are available in accordance with other embodiments of the invention. FIG. 7 illustrates an exemplary user interface for adding/modifying/deleting rows in the Audit Table, according to an embodiment of the invention.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method, comprising:
   receiving, by a switch provider comprising one or more computers, a first claim submission from a pharmacy computer, wherein the first claim submission includes at least one identifier, a prescribed quantity, and days supply for a requested drug, the first claim submission designated for a pharmacy benefits manager (PBM) computer for benefits processing, wherein the switch provider is configured to route communications between the pharmacy computer and the pharmacy benefits manager (PBM) computer;
   accessing, by the switch provider using at least a portion of the at least one identifier for the requested drug, a Multiple Package Edit (MPE) table to obtain package size information for the requested drug;
   determining, by the switch provider whether the prescribed quantity in the first claim submission matches the obtained package size information or a multiple of the obtained package size information;
   accessing, by the switch provider using at least a portion of the at least one identifier for the requested drug, an Audit table to obtain a daily dose for the requested drug, wherein the MPE table and Audit table are maintained independently of each other;
   calculating, by the switch provider, a prescribed daily dose by dividing the prescribed quantity by the days supply;
   determining, by the switch provider, whether the calculated daily dose matches the obtained daily dose or a multiple of the obtained daily dose;
   determining, by the switch provider, that the first claim submission includes an error in at least one of the prescribed quantity or the calculated daily dose; and
   transmitting, by the switch provider to the pharmacy computer, a rejection of the first claim submission, wherein the rejection identifies the determined error in at least one of the prescribed quantity or the calculated daily dose, the rejection further resulting in the first claim submission not being delivered by the switch provider to the pharmacy benefits manager (PBM) computer for adjudication.

2. The method of claim 1, further comprising rejecting the first claim submission upon determining that the first claim submission includes the error.

3. The method of claim 2, wherein the rejection of the first claim submission prevents the first claim submission from being routed to the pharmacy benefits manager (PBM) computer for benefits determination.

4. The method of claim 1, further comprising receiving, by the switch provider, a second claim submission from the pharmacy computer, wherein the second claim submission corrects the error determined in the first claim submission.

5. The method of claim 4, further comprising routing, by the switch provider, the second claim submission to the pharmacy benefits manager (PBM) computer for benefits determination.

6. The method of claim 1, wherein prior to accessing the MPE table or the Audit table, the method further includes:
   determining, by the switch provider, that the requested drug of the first claim submission is not identified in a user table for use in verifying one or more of package size, quantity, or days supply for one or more drugs, wherein the user table includes pharmacy-supplied drug information supplied by a pharmacy associated with the pharmacy computer.

7. The method of claim 6, further comprising:
   receiving, by the switch provider, a second claim submission from the pharmacy computer, wherein the second claim submission includes at least one second identifier, a prescribed second quantity, and second days supply for a requested second drug;
   determining, by the switch provider, that the requested second drug of the second claim submission is identified in the user table for use in verifying one or more of package size, quantity, or days supply for one or more drugs, wherein the user table is maintained by a pharmacy associated with the pharmacy computer,
   wherein the user table is selected to verify a package size, quantity, or days supply associated with the second claim submission; and
   wherein the selection of the user table results in bypassing at least one of the MPE table or Audit table for purposes of determining whether the second claim submission includes any error in package size, quantity, or days supply,
   wherein the prior step is performed by one or more computers.

8. The method of claim 6, wherein the pharmacy-supplied drug information in the user table includes one or more of: (i) package size, (ii) minimum quantity, (iii) maximum quantity, (iv) minimum days supply, (v) maximum days supply, or (vi) multiple package screening information.

9. The method of claim 1, wherein the at least one drug identifier includes at least one of (i) a National Drug Code (NDC) number, or (ii) the NDC number and a Generic Code Number (GCN).

10. The method of claim 1, wherein the audit table and the MPE table are maintained by a service provider.

11. A system, comprising:
    at least one memory for storing computer-executable instructions;
    at least one processor in communication with the memory, wherein the at least one processor forms part of one or more computers of a switch provider configured to route communications between a pharmacy computer and a pharmacy benefits manager (PBM) computer, wherein the at least one processor is operative to execute the computer-executable instructions to:
    receive a first claim submission from a pharmacy computer, wherein the first claim submission includes at least one identifier, a quantity, and days supply for a requested drug, the first claim submission designated for the pharmacy benefits manager (PBM) computer for benefits processing;
    access, using at least a portion of the at least one identifier for the requested drug, an Audit table to obtain a daily dose for the requested drug, wherein the MPE table and Audit table are maintained independently of each other;

calculate a prescribed daily dose by dividing the prescribed quantity by the days supply;

determine whether the calculated daily dose matches the obtained daily dose or a multiple of the obtained daily dose;

determine that the first claim submission includes an error in at least one of the prescribed quantity or the calculated daily dose; and transmit, to the pharmacy computer, a rejection of the first claim submission, wherein the rejection identifies the determined error in at least one of the prescribed quantity or the calculated daily dose, the rejection further resulting in the first claim submission not being delivered by the switch provider to the pharmacy benefits manager (PBM) computer for adjudication.

12. The system of claim 11, wherein the processor is further operative to execute the computer-executable instructions to reject the first claim submission upon determining that the first claim submission includes the error.

13. The system of claim 12, wherein the rejection of the first claim submission prevents the first claim submission from being routed to the pharmacy benefits manager (PBM) computer for benefits determination.

14. The system of claim 11, wherein the processor is further operative to execute the computer-executable instructions to receive a second claim submission from the pharmacy computer, wherein the second claim submission corrects the error determined in the first claim submission.

15. The system of claim 14, wherein the second claim submission is routed to the pharmacy benefits manager (PBM) computer for benefits determination.

16. The system of claim 11, wherein prior to accessing the MPE table or the Audit table, the method further includes:

determining that the requested drug of the first claim submission is not identified in a user table for use in verifying one or more of package size, quantity, or days supply for one or more drugs, wherein the user table includes pharmacy-supplied drug information supplied by a pharmacy associated with the pharmacy computer.

17. The system of claim 16, wherein the processor is further operative to execute the computer-executable instructions to:

receive a second claim submission from the pharmacy computer, wherein the second claim submission includes at least one second identifier, a prescribed second quantity, and second days supply for a requested second drug;

determine that the requested second drug of the second claim submission is identified in the user table for use in verifying one or more of package size, quantity, or days supply for one or more drugs, wherein the user table is maintained by a pharmacy associated with the pharmacy computer, wherein the user table is selected to verify a package size, quantity, or days supply associated with the second claim submission; and wherein the selection of the user table results in bypassing at least one of the MPE table or audit table for purposes of determining whether the second claim submission includes any error in package size, quantity, or days supply.

18. The system of claim 16, wherein the pharmacy-supplied information in the user table includes one or more of: (i) package size, (ii) minimum quantity, (iii) maximum quantity, (iv) minimum days supply, (v) maximum days supply, or (vi) multiple package screening information.

19. The system of claim 11, wherein the at least one drug identifier includes at least one of (i) a National Drug Code (NDC) number, or (ii) the NDC number and a Generic Code Number (GCN).

20. The system of claim 11, wherein the audit table and the MPE table are maintained by a service provider.

* * * * *